US00PP36927P2

(12) United States Plant Patent
Beers

(10) Patent No.: US PP36,927 P2
(45) Date of Patent: Sep. 2, 2025

(54) ***GERBERA* PLANT NAMED 'Hilswebla'**

(50) Latin Name: *Gerbera hybrida*
Varietal Denomination: Hilswebla

(71) Applicant: HilverdaFlorist B.V., De Kwakel (NL)

(72) Inventor: Martin Beers, Hoofddorp (NL)

(73) Assignee: HILVERDAFLORIST B.V., De Kwakel (NL)

( * ) Notice: Subject to any disclaimer, the term of this patent is extended or adjusted under 35 U.S.C. 154(b) by 0 days.

(21) Appl. No.: 18/816,523

(22) Filed: Aug. 27, 2024

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./357
See application file for complete search history.

*Primary Examiner* — Susan McCormick Ewoldt
(74) *Attorney, Agent, or Firm* — C. Anne Whealy

(57) ABSTRACT

A new and distinct cultivar of *Gerbera* plant named 'Hilswebla', characterized by its compact, broadly upright and uniformly mounding plant habit; moderately vigorous growth habit and moderate growth rate; dense and bushy appearance; long flowering period; numerous large semi-double inflorescences with bright yellow and reddish orange bi-colored ray florets and bright yellow-colored disc florets; upright and moderately strong peduncles; and good garden performance and relatively tolerant to low temperatures.

1 Drawing Sheet

Botanical designation: *Gerbera hybrida.*
Cultivar denomination: 'HILSWEBLA'.

BACKGROUND OF THE INVENTION

The present invention relates to a new and distinct cultivar of *Gerbera* plant, botanically known as *Gerbera hybrida*, commercially produced as a container and garden plant and hereinafter referred to by the cultivar name 'Hilswebla'.

The new *Gerbera* plant is a product of a planned breeding program conducted by the Inventor in De Kwakel, The Netherlands. The objective of the breeding program is to create new compact *Gerbera* plants with numerous attractive inflorescences, resistance to low temperatures and good garden performance.

The new *Gerbera* plant originated from a cross-pollination in March, 2020 of a proprietary selection of *Gerbera hybrida* identified as code number 18T2083, not patented, as the female, or seed, parent with a proprietary selection of *Gerbera hybrida* identified as code number 18T2082, not patented, as the male, or pollen, parent. The new *Gerbera* plant was discovered and selected as a single flowering plant from within the progeny of the stated cross-pollination in a controlled greenhouse environment in De Kwakel, The Netherlands during the summer of 2021.

Asexual reproduction of the new *Gerbera* plant by vegetative terminal cuttings and in vitro meristem culture since the autumn of 2021 in De Kwakel, The Netherlands, has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilswebla'. These characteristics in combination distinguish 'Hilswebla' as a new and distinct *Gerbera* plant:

1. Compact, broadly upright and uniformly mounding plant habit.
2. Moderately vigorous growth habit and moderate growth rate.
3. Dense and bushy appearance.
4. Long flowering period.
5. Numerous large semi-double inflorescences with bright yellow and reddish orange bi-colored ray florets and bright yellow-colored disc florets.
6. Upright and moderately strong peduncles.
7. Good garden performance and relative tolerance to low temperatures.

Plants of the new *Gerbera* differ primarily from plants of the female parent selection in the following characteristics:

1. Leaves of plants of the new *Gerbera* are darker green in color than leaves of plants of the female parent selection.
2. Plants of the new *Gerbera* have larger inflorescences than plants of the female parent selection.
3. Inflorescences of plants of the new *Gerbera* are semi-double-types whereas inflorescences of plants of the female parent selection are single-types.

Plants of the new *Gerbera* differ primarily from plants of the male parent selection leaf color as leaves of plants of the new *Gerbera* are darker green in color than leaves of plants of the male parent selection.

Plants of the new *Gerbera* can be compared to plants of the *Gerbera hybrida* 'Sweet Sunset', not patented. In side-by-side comparisons, plants of the new *Gerbera* differ from plants of 'Sweet Sunset' in the following characteristics:

1. Inflorescences of plants of the new *Gerbera* are semi-double-types whereas inflorescences of plants of 'Sweet Sunset' are single-types.
2. Ray florets of plants of the new *Gerbera* are bright yellow and reddish orange bi-colored whereas ray florets of plants of 'Sweet Sunset' are orange to dark orange in color.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant. The photograph is a side perspective view of a typical flowering plant of 'Hilswebla' grown in a container.

DETAILED BOTANICAL DESCRIPTION

The aforementioned photograph and following observations and measurements describe plants grown during the summer in 19-cm containers in a glass-covered greenhouse in De Kwakel, The Netherlands and under cultural practices typical of commercial garden *Gerbera* production. During the production of the plants, day temperatures ranged from 16° C. to 20° C. and night temperatures ranged from 16° C. to 18° C. Plants were six months old when the photograph was taken and one year old when the description was taken. In the following description, color references are made to The Royal Horticultural Society Colour Chart, 2015 Edition, except where general terms of ordinary dictionary significance are used.

Botanical classification: *Gerbera hybrida* 'Hilswebla'.

Parentage:

*Female, or seed, parent*.—Proprietary selection of *Gerbera hybrida* identified as code number 18T2083, not patented.

*Male, or pollen, parent*.—Proprietary selection of *Gerbera hybrida* identified as code number 18T2082, not patented.

Propagation:

*Type*.—By cuttings and in vitro meristem culture.

*Time to initiate roots, by cuttings, summer and winter*.—About 3.5 weeks at minimum temperatures of 20° C.

*Time to initiate roots, by tissue culture, summer and winter*.—About 2.5 to 3 weeks at minimum temperatures of 20° C.

*Time to produce a rooted young plant, by cuttings, summer and winter*.—About 3.5 weeks after rooting, at temperatures about 20° C. to 26° C.

*Time to produce a rooted young plant, by tissue culture, summer and winter*.—About five to six weeks at temperatures about 20° C. to 26° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; compact, broadly upright and uniformly mounding; roughly flattened globular in shape; numerous leaves arranged in basal rosettes; dense and bushy habit; inflorescences held above the foliar plane on erect and strong basal peduncles; moderately vigorous and moderate growth rate; inflorescences held above the foliar plane

*Plant height, soil level to top of foliar plane*.—About 25.2 cm.

*Plant height, soil level to top of inflorescences*.—About 35 cm.

*Plant width or spread*.—About 43 cm.

Leaf description:

*Arrangement*.—Alternate, basal, simple.

*Length*.—About 20.4 cm.

*Width*.—About 13.6 cm.

*Shape*.—Broadly ovate in overall outline; runcinate.

*Apex*.—Rounded to broadly and bluntly acute.

*Base*.—Short attenuate.

*Margin*.—Coarsely and irregularly angulate.

*Texture and luster, upper surface*.—Smooth, glabrous except for sparse pubescence along main vein; moderately glossy.

*Texture and luster, lower surface*.—Densely pubescent, matte to slightly glossy.

*Venation pattern*.—Pinnate.

*Color*.—Developing leaves, upper and lower surfaces: Close to 143A. Fully expanded leaves, upper surface: Close to NN137A; venation, close to 144A. Fully expanded leaves, lower surface: Close to 147B; venation, close to 144A.

*Petioles*.—Length: About 5.6 cm. Diameter: About 4.5 mm. Texture and luster, upper and lower surfaces: Densely pubescent; slightly glossy. Strength: Moderately strong to strong. Color, upper surface: Close to 144A; towards the margins, close to NN137C. Color, lower surface: Close to 144A.

Inflorescence description:

*Appearance*.—Composite inflorescence form with oblanceolate to narrowly oblanceolate-shaped ray florets; solitary inflorescences borne on upright and moderately strong peduncles and held above the foliar plane; ray, trans and disc florets arranged acropetally on a capitulum; inflorescences face mostly upright.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about three weeks on the plant; inflorescences persistent.

*Quantity of inflorescences*.—Freely flowering habit with about nine developing and fully developed inflorescences at one time.

*Inflorescence buds*.—Height: About 1.4 cm. Diameter: About 1.8 cm. Shape: Flattened hemispherical. Texture and luster: Densely pubescent; matte. Color: Close to 137B; immature ray florets, close to 150A and 150B.

*Inflorescence size*.—Diameter: About 7.4 cm. Depth (height): About 2.6 cm. Diameter of disc: About 1.6 cm.

*Receptacles*.—Height: About 5 mm. Diameter: About 1.3 cm. Shape: Flattened globular. Color: Close to 157C with margins, close to 144C.

*Ray florets*.—Quantity and arrangement: About 72 per inflorescence arranged in about two whorls. Orientation: Proximally, about 70° from horizontal; distally, close about 30° from horizontal. Length: About 3.7 cm. Width: About 7 mm. Shape: Oblanceolate to narrowly oblanceolate. Apex: Minutely emarginate. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Proximally, close to a blend of N30A and N30B; distally, close to 12A. When opening, lower surface: Close to 12A. Fully opened, upper surface: Proximally, close to 34A; distally and narrow marginal edges, close to a blend of 12A and 13A; venation, similar to lamina colors; color does not change with subsequent development. Fully opened, lower surface: Close to 13B occasionally tinged with close to 28A and 28B; venation, similar to lamina colors; color does not change with subsequent development.

*Trans florets*.—Quantity and arrangement: About 75 per inflorescence arranged in about three whorls. Orientation: About 70° from horizontal. Length: About 1.5 cm. Width: About 5 mm. Shape: Oblanceolate; lower 67% is fused and upper 33% has three unequal lobes: a central lobe, about 2 mm in width and two lateral lobes, about 0.5 mm in width. Apex: Lobes, acute. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to 13A; centers, slightly tinged with close to N25A. When opening, lower surface: Close to 13B. Fully opened, upper surface: Proximally, close to 26A; distally, close to 13A; venation, similar to lamina colors; color does not change with subsequent development. Fully opened, lower surface: Close to 13C; venation, similar to lamina colors; color does not change with subsequent development.

*Disc florets*.—Quantity and arrangement: About 300 disc florets at center of the inflorescence arranged in about a six-whorl spiral; lower 80% of the disc floret is fused. Length: About 1.2 cm. Width: About 1.5 mm. Shape: Tubular with two or three narrow free lobes; one broader free lobe, about 1 mm in width and one or two narrower free lobes, about 0.5 mm in width. Apex, free lobes: Acute. Base: Fused. Margin, free lobes: Entire; not undulate. Texture, upper surface: Smooth, glabrous; moderately velvety; matte. Texture, lower surface: Smooth, glabrous; slightly velvety; slightly glossy. Color: When opening, inner and outer surfaces: Close to 154C; towards the base, close to 154D. Fully opened, inner and outer surfaces: Close to 13B; towards the base, close to 14D.

*Pappus*.—Quantity of hairs per floret: Numerous. Length: About 7 mm. Diameter: Fine, less than 0.1 mm. Texture and luster: Soft; matte. Color: Close to 161D.

*Phyllaries*.—Quantity and arrangement: About 80 per inflorescence arranged in about three whorls. Length: About 1.2 cm. Width (at base): About 1.5 mm. Shape: Narrowly lanceolate. Apex: Narrowly acute. Base: Cuneate. Margin: Entire. Texture and luster, upper surface: Smooth, glabrous; moderately glossy. Texture and luster, lower surface: Moderately to densely pubescent; matte. Color, upper surface: Close to 143C. Color, lower surface: Close to 137B and 137C.

*Peduncles*.—Length: About 28.5 cm. Diameter: Proximally, about 7 mm; distally, about 4 mm. Strength: Moderately strong. Angle: Erect to about 10° from vertical. Texture and luster: Densely pubescent; moderately glossy. Color: Close to 144B; distally, close to 146B.

*Reproductive organs*.—Androecium (present on disc florets only): Quantity per floret: Five. Filament length: About 4 mm. Filament color: Close to 12B. Anther shape: Linear; basifixed. Anther size: About 3 mm by 0.3 mm. Anther color: Close to 13B. Pollen amount: Moderate. Pollen color: Close to 12A. Gynoecium (present on main and trans ray florets): Quantity per floret: One. Pistil length: About 1 cm. Stigma diameter: About 0.3 mm. Stigma shape: Cleft. Stigma color: Close to 12C. Style length: About 1.15 cm. Style color: Close to 12C. Ovary color: Close to 157A.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −6° C. to about 35° C. and to be cold hardy to USDA Hardiness Zone 7.

It is claimed:

1. A new and distinct *Gerbera* plant named 'Hilswebla' as herein illustrated and described.

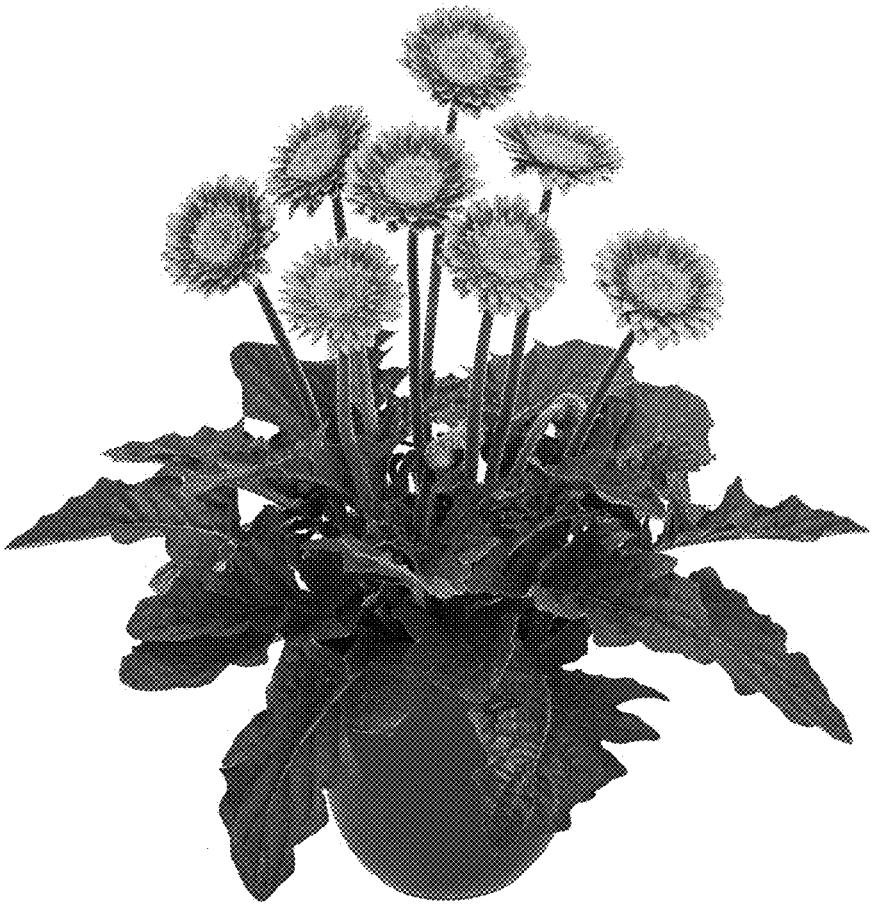

* * * * *